(12) United States Patent
Uneme et al.

(10) Patent No.: US 6,265,582 B1
(45) Date of Patent: Jul. 24, 2001

(54) METHOD FOR PRODUCING ISOUREAS

(75) Inventors: Hideki Uneme; Yasuo Kamiya; Masato Konobe, all of Tsukuba; Junji Yamada, Hikari, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/530,509

(22) PCT Filed: Dec. 22, 1998

(86) PCT No.: PCT/JP98/05804

§ 371 Date: May 1, 2000

§ 102(e) Date: May 1, 2000

(87) PCT Pub. No.: WO99/33809

PCT Pub. Date: Jul. 8, 1999

(30) Foreign Application Priority Data

Dec. 24, 1997 (JP) .................................................. 9-354735
Jul. 31, 1998 (JP) ................................................ 10-217192

(51) Int. Cl.$^7$ ................................................. C07C 277/08
(52) U.S. Cl. ........................... 546/334; 546/329; 548/205
(58) Field of Search ..................... 546/334, 329; 548/203, 205

(56) References Cited

U.S. PATENT DOCUMENTS 5,175,301 12/1992 Minamida et al. .
6,008,363 * 12/1999 Uneme et al. ........................ 546/334

FOREIGN PATENT DOCUMENTS 0376279    7/1990   (EP) .
3-157358   7/1991   (JP) .
WO 97/00867 1/1997  (WO) .

OTHER PUBLICATIONS

J. W. Janus: "O–Alkylation of Urea", Journal of the Chemical Society, 1955, pp. 3551–3552.
N. Heyboer et al.: "Note on The Conversion of The Amino Group of Amino Acids into The Nitroguanidino Group", Recueil Des Travaux Chimiques Des PAYS–BAS, vol. 81,1962, pp. 69–72.

* cited by examiner

Primary Examiner—Jean F. Vollano

(74) Attorney, Agent, or Firm—Wenderoth, Lind & Ponack, L.L.P.

(57) ABSTRACT

The present invention relates to a method for producing a compound of the formula:

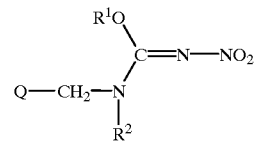

[IV]

wherein $R^1$ is an optionally substituted hydrocarbon group; $R^2$ is H or an optionally substituted hydrocarbon group; and Q is an optionally substituted heterocyclic group, or a salt thereof which comprises subjecting a compound of the formula:

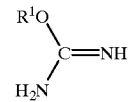

[I]

wherein $R^1$ has the same meaning as defined above, or a salt thereof to a nitration reaction (a), and further subjecting the resulting mixture without isolating/purifying the resulting compound of the formula:

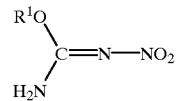

[II]

wherein $R^1$ has the same meaning as defined above, or a salt thereof to a reaction (b) with a compound of the formula:

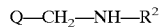

[III]

wherein each symbol has the same meaning as defined above, or a salt thereof. According to the production method of the present invention, a compound [IV] as an intermediate of a guanidine derivative having an excellent insecticidal activity, or a salt thereof can be mass-produced, industrially.

11 Claims, No Drawings

METHOD FOR PRODUCING ISOUREAS

This application is a 371 of PCT/JP98/05804 filed Dec. 22, 1998.

TECHNICAL FIELD

The present invention relates to an improved method for producing intermediates of guanidine derivatives which are useful as insecticides.

BACKGROUND ART

A guanidine derivative having an insecticidal activity and a method for producing the same are disclosed in JP-A-157308/1991. As an improved method for producing the guanidine derivative, a method for producing via an isourea derivative is disclosed in WO97/00867 as shown in the following scheme 1.

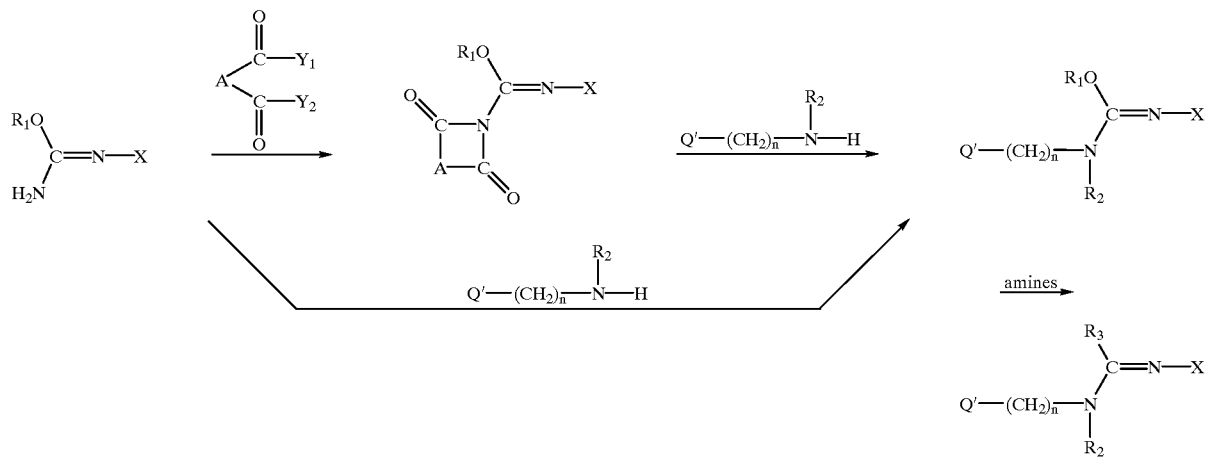

wherein $R_1$ and $R_2$ are the same or different, and each represents a hydrogen atom or an optionally substituted hydrocarbon group; $R_3$ represents an optionally substituted amino group; A represents a divalent hydrocarbon group which may optionally be substituted; Q' represents an optionally substituted heterocyclic group; X represents an electron withdrawing group; $Y_1$ and $Y_2$ are the same or different, and each represents a leaving group; and n represents 0 or 1.

Among the starting materials in the above-mentioned method via the isourea derivative, for example, O-methyl-N-nitroisourea (hereinafter, sometimes abbreviated as MNI) or a salt thereof can be usually produced by nitrating O-methylisourea or a salt thereof (Recueil des Travaux Chimiques des Pays-Bas, Vol.81, pp.69, 1962).

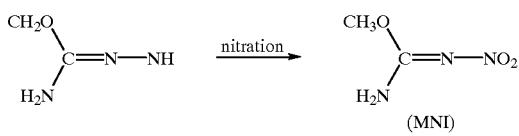

In this method, for example, when MNI is obtained by industrially conducting nitration by using nitric acid in sulfuric acid, pouring the reaction mixture into cold water or ice, or a mixture of water and ice after the completion of the reaction, and cooling the mixture to about −15° C. to separate the resulting MNI by filtration, MNI is obtained in a low yield of about 75% at the maximum by only a post-treatment operation such as separation by filtration because of the water-solubility of MNI. Furthermore, the yield is further lowered by increasing the scale of the reaction. The yield increases to about 90% by extracting from a mother liquor for filtration. However, since the solubility of MNI in a usable extraction solvent is not so high, a large amount of an organic solvent is required and, therefore, the operation becomes complicated and is very disadvantageous from an industrial point of view. In the case of using O-methylisourea monomethyl sulfate as a starting material, this compound can be obtained by the reaction between urea and dimethyl sulfuric acid, but this reaction itself proceeds in a yield of only about 60% (Journal of Chemical Society, Vol.1955, pp.3551) and subsequent post-treatment of nitration requires extraction by solvent. Furthermore, MNI corresponds to a dangerous object V under the Jananese Fire Services Act., and has explosive properties.

DISCLOSURE OF INVENTION

Under these circumstances, an object of the present invention is to provide a method for producing an intermediate of a guanidine derivative which can be advantageously and safely practiced from an industrial point of view.

The present inventors have intensively studied methods for producing N-nitroisoureas such as NMI or a salt thereof and the reaction of subsequent steps to attain the above object.

As a result, the inventors found surprisingly that a compound represented by the formula:

[IV]

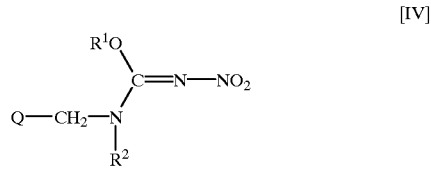

wherein $R^1$ represents an optionally substituted hydrocarbon group; $R^2$ represents a hydrogen atom or an optionally substituted hydrocarbon group; and Q represents an optionally substituted heterocyclic group, or a salt thereof can be produced in a high yield by subjecting a compound represented by the formula:

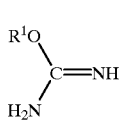
[I]

wherein R¹ has the same meaning as defined above, or a salt thereof to a nitration reaction (a), and further subjecting the resulting mixture without isolating/purifying the resulting compound represented by the formula:

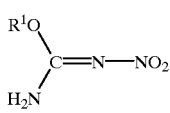
[II]

wherein R¹ has the same meaning as defined above, or a salt thereof to a reaction (b) with a compound represented by the formula:

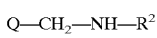
Q—CH₂—NH—R²    [III]

wherein each symbol has the same meaning as defined above, or a salt thereof.

It is not usually expected that the compound [IV] or a salt thereof can be obtained in a high yield regardless of the assumption that by-products produced during the nitration reaction (a), starting materials and a large amount of salts of sulfate and nitrate are present in the reaction system of the reaction (b) of the present invention, that is exactly the surprising result. By means of the experimental operation of the present invention, not only industrial disadvantages of the isolation of N-nitroisoureas such as MNI or salts thereof [i.e. the yield is low only by filtration and, when the extraction is conducted to improve the yield, the post-treatment becomes very complicated] have been solved once for all, but also the safety of the operation has been improved remarkably because N-nitroisoureas such as MNI having a risk of explosion or a salt thereof are not isolated. Furthermore, the present inventors have intensively studied based on such a knowledge, thus completing the present invention.

Namely, the present invention relates to:

[1] a method for producing a compound represented by the formula:

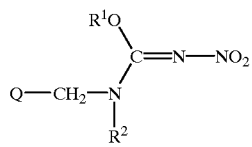
[IV]

wherein R¹ represents an optionally substituted hydrocarbon group; R² represents a hydrogen atom or an optionally substituted hydrocarbon group; and Q represents an optionally substituted heterocyclic group, or a salt thereof which comprises subjecting a compound represented by the formula:

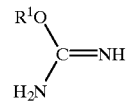
[I]

wherein R¹ has the same meaning as defined above, or a salt thereof to the nitration reaction (a), and further subjecting the resulting mixture without isolating/purifying the resulting compound represented by the formula:

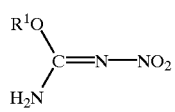
[II]

wherein R¹ has the same meaning as defined above, or a salt thereof to the reaction (b) with a compound represented by the formula:

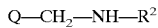
Q—CH₂—NH—R²    [III]

wherein each symbol has the same meaning as defined above, or a salt thereof,

[2] the method as described in [1] above, wherein the nitration reaction (a) is carried out by using nitric acid in the presence of sulfuric acid,

[3] the method as described in [1] above, wherein a degassing treatment under reduced pressure is carried out after the completion of the nitration reaction (a),

[4] the method as described in [1] above, wherein the reaction mixture is diluted with water and/or ice after the completion of nitration reaction (a), and then subjected to the reaction (b),

[5] the method as described in [4] above, wherein a gas which does not interfere with the reaction is bubbled during the dilution of the reaction mixture with water and/or ice,

[6] the method as described in [5] above, wherein the gas which does not interfere with the reaction is air or nitrogen,

[7] the method as described in [4] above, wherein the reaction (b) is carried out under pH 5 to 8,

[8] the method as described in [4] above, wherein the reaction (b) is carried out under pH 6 to 7.5,

[9] the method as described in [1] above, wherein R¹ is a $C_{1-3}$ alkyl group,

[10] the method as described in [1] above, wherein the compound represented by the formula[I] or a salt thereof is O-methylisourea sulfate, O-methylisourea 1/2 sulfate or O-methylisourea monomethyl sulfate, and

[11] the method as described in [1] above, wherein R² is a hydrogen atom and Q is a 6-chloro-3-pyridyl group or a 2-chloro-5-thiazolyl group.

BEST MODE FOR CARRYING OUT THE INVENTION

In the above formulas, the hydrocarbon group in the optionally substituted hydrocarbon group for R¹ or R², includes a saturated or unsaturated aliphatic hydrocarbon group or an aromatic hydrocarbon group.

The saturated or unsaturated hydrocarbon group includes a $C_{1-15}$ alkyl group such as methyl, ethyl, propyl, isopropyl, butyl, isobutyl, s-butyl, t-butyl, pentyl, hexyl, heptyl, octyl, nonyl, decyl, undecyl, dodecyl, tridecyl, tetradecyl or pentadecyl; a $C_{2-10}$ alkenyl group such as vinyl, allyl, 2-methylallyl, 2-butenyl, 3-butenyl or 3-octenyl; a $C_{2-10}$ alkynyl group such as ethynyl, 2-propynyl or 3-hexynyl; a $C_{3-10}$ cycloalkyl group such as cyclopropyl, cyclobutyl, cyclopentyl or cyclohexyl; or a $C_{3-10}$ cycloalkenyl group such as cyclopropenyl, cyclopentenyl or cyclohexenyl.

The aromatic hydrocarbon group includes a $C_{6-14}$ aryl group such as phenyl, naphthyl, azulenyl, anthryl or phenanthryl; or a $C_{7-11}$ aralkyl group such as a phenyl-$C_{1-4}$ alkyl group (e.g. benzyl, phenylethyl).

The heterocyclic group in the optionally substituted heterocyclic group for Q includes a 3- to 8-membered heterocyclic group containing 1 to 5 hetero atoms selected from oxygen atom, sulfur atom and nitrogen atom, or its condensed heterocyclic group with a benzene ring or a 3- to 8-membered heterocyclic ring containing 1 to 5 hetero atoms selected from oxygen atom, sulfur atom and nitrogen atom, such as thienyl (e.g. 2- or 3-thienyl), tetrahydrothienyl (e.g. 2- or 3-tetrahydrothienyl), furyl (e.g. 2- or 3-furyl), tetrahydrofuryl (e.g. 2- or 3-tetrahydrofuryl), pyrrolyl (e.g. 1-, 2- or 3-pyrrolyl), pyridyl (e.g. 2-, 3- or 4-pyridyl), oxazolyl (e.g. 2-, 4- or 5-oxazolyl), thiazolyl (e.g. 2-, 4- or 5-thiazolyl), pyrazolyl (e.g. 1-, 3-, 4- or 5-pyrazolyl), imidazolyl (e.g. 1-, 2-, 4- or 5-imidazolyl), isoxazolyl (e.g. 3-, 4- or 5-isoxazolyl), isothiazolyl (e.g. 3-, 4- or 5-isothiazolyl), oxadiazolyl [e.g. 3- or 5-(1,2,4-oxadiazolyl), 2- or 5-(1,3,4-oxadiazolyl)], thiadiazolyl [e.g. 3- or 5-(1,2,4-thiadiazolyl), 2- or 5-(1,3,4-thiadiazolyl), 4- or 5-(1,2,3-thiadiazolyl), 3- or 4-(1,2,5-thiadiazolyl)], triazolyl [e.g. 1-, 4- or 5-(1,2,3-triazolyl), 1-, 3- or 5-(1,2,4-triazolyl)], tetrazolyl [e.g. 1- or 5-(1H-tetrazolyl), 2- or 5-(2H-tetrazolyl)], pyridyl in which the nitrogen atom is oxidized (e.g. N-oxido-2-, 3- or 4-pyridyl), pyrimidinyl (e.g. 2-, 4- or 5-pyrimidinyl), pyrimidinyl in which one or both of the nitrogen atoms are oxidized (e.g. N-oxido-2-, 4-, 5- or 6-pyrimidinyl), pyridazinyl (e.g. 3- or 4-pyridazinyl), pyrazinyl, pyridazinyl in which one or both of the nitrogen atoms are oxidized (e.g. N-oxido-3-, 4-, 5- or 6-pyridazinyl), indolyl, benzofuryl, benzothiazolyl, benzoxazolyl, triazinyl, oxotriazinyl, imidazo[1,2-a]pyridinyl, tetrazolo[1,5-b]pyridazinyl, triazolo[4,5-b]pyridazinyl, oxoimidazinyl, dioxotriazinyl, chromanyl, benzoimidazolyl, quinolyl, isoquinolyl, cinnolyl, phthalazinyl, quinazolinyl, quinoxalinyl, indolizinyl, quinolizinyl, naphthyridinyl (e.g. 1,8-naphthyridinyl), purinyl, pteridinyl, dibenzofuranyl, carbazolyl, acridinyl, phenanthridinyl, phenazinyl, phenothiazinyl, phenoxazinyl, aziridinyl, azetidinyl, pyrrolinyl, pyrrolidinyl, piperidinyl, pyranyl, thiopyranyl, dioxanyl (e.g. 1,4-dioxanyl), morpholinyl (e.g. morpholino), thiomorpholinyl, thiazinyl (e.g. 1,4-thiazinyl, 1,3-thiazinyl), and piperazinyl.

Each of the above-mentioned hydrocarbon groups and heterocyclic groups may have the same or different one to five substituents, preferably one to three substituents, in substitutable positions.. Moreover, when the substituent is halogen, each hydrocarbon group or heterocyclic groups may optionally be substituted with up to the maximum possible number of halogen atoms. The preferred substituent includes a $C_{1-15}$ alkyl group such as methyl, ethyl, propyl, isopropyl, butyl, isobutyl, s-butyl, t-butyl, pentyl, hexyl, heptyl, octyl, nonyl, decyl, undecyl, dodecyl, tridecyl, tetradecyl or pentadecyl; a $C_{3-10}$ cycloalkyl group such as cyclopropyl, cyclobutyl, cyclopentyl or cyclohexyl; a $C_{2-10}$ alkenyl group, such as vinyl, allyl, 2-methylallyl, 2-butenyl, 3-butenyl or 3-octenyl; a $C_{2-10}$ alkynyl group such as ethynyl, 2-propynyl or 3-hexynyl; a $C_{3-10}$ cycloalkenyl group such as cyclopropenyl, cyclopentenyl or cyclohexenyl; a $C_{6-10}$ aryl group such as phenyl or naphthyl; a $C_{7-11}$ aralkyl group such as a phenyl-$C_{1-4}$ alkyl group (e.g. benzyl or phenylethyl); nitro; nitroso; hydroxyl; mercapto; cyano; oxo; thioxo; carbamoyl; a mono- or di-$C_{1-6}$ alkylcarbamoyl group such as methylcarbamoyl or dimethylcarbamoyl; a $C_{6-14}$ arylcarbamoyl group such as phenylcarbamoyl; carboxyl; a $C_{2-5}$ alkoxycarbonyl group such as methoxycarbonyl or ethoxycarbonyl; a $C_{6-14}$ aryloxy-carbonyl group such as phenoxycarbonyl; sulfo; halogen such as fluorine, chlorine, bromine or iodine; a $C_{1-4}$ alkoxy group such as methoxy, ethoxy, propoxy, isopropoxy, butoxy, isobutoxy, s-butoxy or t-butoxy; a $C_{6-10}$ aryloxy group such as phenoxy; a $C_{1-4}$ alkylthio group such as methylthio, ethylthio, propylthio, isopropylthio, butylthio, isobutylthio, s-butylthio or t-butylthio; a $C_{6-10}$ arylthio group such as phenylthio; a $C_{1-4}$ alkylsulfinyl group such as methylsulfinyl, ethylsulfinyl, propylsulfinyl, isopropylsulfinyl, butylsulfinyl, isobutylsulfinyl, s-butylsulfinyl or t-butylsulfinyl; a $C_{6-10}$ arylsulfinyl group such as phenylsulfinyl; a $C_{1-4}$ alkylsulfonyl group such as methylsulfonyl, ethylsulfonyl, propylsulfonyl, isopropylsulfonyl, butylsulfonyl, isobutylsulfonyl, s-butylsulfonyl or t-butylsulfonyl; a $C_{6-10}$ arylsulfonyl group such as phenylsulfonyl; a $C_{1-4}$ alkoxysulfonyl group such as methoxysulfonyl, ethoxysulfonyl, propoxysulfonyl, isopropoxysulfonyl, butoxysulfonyl, isobutyloxysulfonyl, s-butoxysulfonyl or t-butoxysulfonyl; a $C_{6-10}$ aryloxysulfonyl group such as phenoxysulfonyl; amino; a $C_{1-11}$ carboxylic acylamino group such as a $C_{1-6}$ alkanoylamino group (e.g. acetylamino or propionylamino) or a $C_{6-10}$ arylcarbonylamino group (e.g. benzoylamino); a mono- or di-$C_{1-4}$ alkylamino group such as methylamino, ethylamino, propylamino, isopropylamino, butylamino, dimethylamino or diethylamino; a $C_{3-6}$ cycloalkylamino group such as cyclohexylamino; a $C_{6-10}$ arylamino group such as anilino; a tri-substituted silyl group such as a tri-$C_{1-6}$ alkylsilyl group (e.g. trimethylsilyl or t-butyldimethylsilyl), a tri-$C_{6-10}$ arylsilyl group (e.g. triphenylsilyl), or t-butylmethoxyphenylsilyl; a $C_{1-11}$ carboxylic acyl group such as a $C_{1-6}$ alkanoyl group (e.g. formyl or acetyl), or a $C_{6-10}$ aryl-carbonyl group (e.g. benzoyl); or a 3- to 6-membered heterocyclic group containing 1 to 5 hetero atoms selected from oxygen, sulfur and nitrogen, and its condensed heterocyclic group with a benzene ring or a 3- to 6-membered heterocyclic ring containing 1 to 5 hetero atoms selected from oxygen, sulfur and nitrogen, such as thienyl (e.g. 2- or 3-thienyl), furyl (e.g. 2- or 3-furyl), pyrrolyl (e.g. 1-, 2- or 3-pyrrolyl), pyridyl (e.g. 2-, 3- or 4-pyridyl), oxazolyl (e.g. 2-, 4- or 5-oxazolyl), thiazolyl (e.g. 2-, 4- or 5-thiazolyl), pyrazolyl (e.g. 1-, 3-, 4- or 5-pyrazolyl), imidazolyl (e.g. 1-, 2-, 4- or 5-imidazolyl), isoxazolyl (e.g. 3-, 4- or 5-isoxazolyl), isothiazolyl (e.g. 3-, 4- or 5-isothiazolyl), triazolyl (e.g. 1,2,3- or 1,2,4-triazolyl), pyrimidinyl (e.g. 2-, 4- or 5-pyrimidinyl), benzothiazolyl, benzoxazolyl, triazinyl, oxiranyl, aziridinyl, pyrrolidinyl, piperidinyl, piperazinyl, morpholinyl, thiomorpholinyl, benzimidazolyl, quinolyl or isoquinolyl. When two or more substituents are present, two of the substituents may form a divalent group such as a $C_{1-6}$ alkylene group (e.g. methylene, ethylene, trimethylene, tetramethylene or propenylene), 3-oxapentamethylene, vinylene, benzylidene, methylenedioxy, 2-thiatrimethylene, oxalyl, malonyl, succinyl, maleoyl, phthaloyl, oxygen, sulfur, imino, azo or hydrazo.

When any of these substituents is aryl, aralkyl, cycloalkyl, cycloalkenyl, aryloxy, arylthio, arylsulfinyl, arylsulfonyl, arylcarbamoyl, aryloxycarbonyl, aryloxysulfonyl, arylamino, cycloalkylamino, carboxylic acyl, carboxylic acylamino, tri-substituted silyl, heterocyclic group or divalent group, these substituents may further have 1 to 5 substituents such as aforementioned halogen atom, hydroxyl, nitro, cyano, a $C_{1-4}$ alkyl group (e.g. methyl, ethyl, propyl, isopropyl, butyl, isobutyl, s-butyl or t-butyl), a $C_{2-4}$ alkenyl group (e.g. vinyl or allyl), a $C_{2-4}$ alkynyl group (e.g. ethynyl or 2-propynyl), phenyl, a $C_{1-4}$ alkoxy group (e.g. methoxy or ethoxy), phenoxy, a $C_{1-4}$ alkylthio group (e.g. methylthio or ethylthio) and phenylthio, and particularly in case of halogen, the above-mentioned substituents may optionally be substituted with up to the maximum possible number of halogen atoms.

When any of these substituents is alkyl, alkenyl, alkynyl, alkoxy, alkylthio, alkylsulfinyl, alkylsulfonyl, alkylcarbamoyl, alkoxycarbonyl, alkoxysulfonyl, amino or alkylamino, their substituents may further have 1 to 5 substituents such as aforementioned halogen atom, hydroxyl, nitro, cyano, a $C_{1-4}$ alkoxy group (e.g. methoxy or ethoxy) and a $C_{1-4}$ alkylthio group (e.g. methylthio or ethylthio), and particularly in case of halogen, the above-mentioned substituents may optionally be substituted with up to the maximum possible number of halogen atoms.

$R^1$ is preferably a saturated or unsaturated aliphatic hydrocarbon group and more preferably a $C_{1-15}$ alkyl group. Particularly preferred are $C_{1-3}$ alkyl groups, methyl being most preferred.

$R^2$ is preferably a hydrogen atom, or a saturated or unsaturated aliphatic hydrocarbon group. Particularly preferred are a hydrogen atom and a $C_{1-15}$ alkyl group. Still more preferred are a hydrogen atom and a $C_{1-4}$ alkyl group, a hydrogen atom being most preferred.

Q is preferably a 5- or 6-membered heterocyclic group containing at least one nitrogen, oxygen or sulfur atom as a ring-constituent atom, which may optionally be halogenated. Particularly preferred are halogenated pyridyl group, halogenated thiazolyl group and tetrahydrofuryl group. Specifically, 6-chloro-3-pyridyl group, 2-chloro-5-thiazolyl group and 3-tetrahydrofuryl group are most preferred.

Salts of the compounds [I], [II], [III] and [IV] represented by the above formulas [I], [II], [III] and [IV] may be agrochemically acceptable salts and include, for example, salts with inorganic acids such as hydrochloric acid, hydrobromic acid, hydroiodide acid, phosphoric acid, sulfuric acid and perchloric acid; and salts with organic acids such as formic acid, acetic acid, tartaric acid, malic acid, citric acid, oxalic acid, succinic acid, benzoic acid, picric acid, methanesulfonic acid and p-toluenesulfonic acid. Among them, hydrochloride and sulfate are preferable. In case of the compound [I], sulfate ($R^1OC(NH_2)$=$NH.H_2SO_4$), 1/2 sulfate ($R^1OC(NH_2)$=$NH.1/2H_2SO_4$) or monomethyl sulfate ($R^1OC(NH_2)$=$NH.MeHSO_4$) are particularly preferable.

The method of the present invention can be carried out, for example, according to the reaction conditions described below. When the product is obtained in the form of a free compound by the production method described below, the resulting compound can be converted into a salt as described above according to a conventional method. On the other hand, when the product is obtained in the form of a salt by the production method described below, the resulting compound can be converted into a free compound according to a conventional method. Furthermore, when the starting compound can be converted into a salt as described above, it can also be used as not only a free compound but also a salt. Accordingly, the starting material and reaction product thereof used in the method described below may include salts thereof (e.g. salts with acid as described for the above compound [I]).

Reaction (a)

A mixture containing the compound [II] (e.g. MNI) or a salt thereof can be obtained by nitrating the compound [I] or a salt thereof using an appropriate nitrating agent.

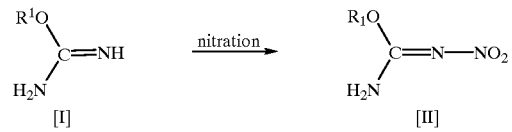

As the nitrating agent, 60 to 100% nitric acid is commonly used, but an alkali metal nitrate such as sodium nitrate and potassium nitrate; an alkyl nitrate such as ethyl nitrate and amyl nitrate; and nitronium tetrafluoroborate ($NO_2BF_4$) and nitronium trifluoromethanesulfonate ($NO_2CF_3SO_3$) may be used. Particularly, 90% or more nitric acid is preferable.

The nitrating agent can be used in a proportion of about 1.0 to about 20 equivalents with respect to the amount of the compound [I]. The proportion is preferably from about 1.5 to about 10 equivalents in case of using nitric acid. The proportion is preferably from about 1.5 to about 3 equivalents in case of using 90% or more nitric acid.

This reaction may be conducted in the absence of the solvent, but is usually conducted in the presence of an acidic solvent such as sulfuric acid, acetic acid, acetic anhydride, trifluoroacetic acid or trifluoromethanesulfonic acid. A solvent which does not interfere with the reaction, or a mixture thereof may be used, if desired. As the solvent, for example, there can be used aromatic hydrocarbons such as benzene, toluene, xylene, etc.; halogenated hydrocarbons such as dichloromethane, chloroform, 1,2-dichloroethane, carbon tetrachloride, etc.; saturated hydrocarbons such as hexane, heptane, cyclohexane, etc.; ethers such as diethyl ether, tetrahydrofuran, dioxane, etc.; ketones such as acetone, methyl ethyl ketone, etc.; nitrites such as acetonitrile, propionitrile, etc.; sulfoxides such as dimethylsulfoxide, etc.; acid amides such as N,N-dimethylformamide, N,N-dimethylacetoamide, etc.; esters such as ethyl acetate, butyl acetate, etc.; alcohols such as methanol, ethanol, propanol, isopropanol, etc.; and water; in addition to the acidic solvents described above. These solvents can be used alone, or two or more kinds of them may be mixed in an appropriate proportion, for example, about 1:1 to about 1:10 (by volume). When the reaction mixture is not homogeneous, the reaction may be conducted in the presence of a phase transfer catalyst such as quaternary ammonium salts such as triethylbenzyl ammonium chloride, tri-n-octylmethyl ammonium chloride, trimethyldecyl ammonium chloride, tetramethyl ammonium chloride, tetramethyl ammonium bromide, cetylpyridinium bromide, etc. and crown ethers. A particularly preferable solvent is sulfuric acid.

The reaction temperature of the present reaction is normally in a range from about -50 to about 100° C. and preferably from about -20 to about 30° C. The reaction time is in a range from about 10 minutes to about 10 hours, and preferably from about 30 minutes to about 3 hours.

In this reaction, a degassing treatment is preferably conducted under reduced pressure after the completion of the reaction. The pressure reducing treatment may be occasionally conducted during the reaction. The degree of reduced pressure may be less than an atmospheric pressure at that time, but usually in a range from about 500 to about 1 mmHg, and preferably from about 100 to about 10 mmHg.

The temperature, at which the pressure reducing treatment is conducted, is normally from about -20 to about 100° C., and preferably from about 10 to about 60° C. The time treated under reduced pressure is normally from about 5 minutes to about 1 day, and preferably from about 20 minutes to about 5 hours.

A mixture containing the compound [II] or a salt thereof can be obtained by diluting the reaction mixture with water and/or ice after the completion of the reaction. Specifically, the mixture containing the compound [II] or a salt thereof can be obtained by pouring the reaction mixture into cold water or ice or mixture of water and ice after the completion of the reaction. Dilution of the reaction mixture is conducted with taking care of heat generation in case of using sulfuric acid as the solvent. The temperature of this dilution procedure is usually from about -20 to about 60° C., and preferably from about -10 to about 30° C.

In this case, the reaction mixture preferably is poured into water and/or ice with bubbling a gas, which does not interfere with the reaction. The gas to be bubbled is not specifically limited, as far as it does not interfere with the reaction, and examples thereof include air, nitrogen, helium, argon, carbon dioxide and the like. Particularly preferable gas is air or nitrogen. The gas may be continuously bubbled while pouring the reaction mixture and, furthermore, the bubbling may be continued during a neutralizing operation described below. Occasionally, the gas can be bubbled while the reaction (b) is carried out. The amount of the gas to be bubbled is preferably from about 10 to about 1/10 times as much as the whole volume of reaction solution per minute.

Reaction (b)

The compound [IV] or a salt thereof can be produced by further reacting the compound [III] or a salt thereof with the reaction mixture containing the above compound [II] or a salt thereof without isolating/purifying the compound [II] or a salt thereof.

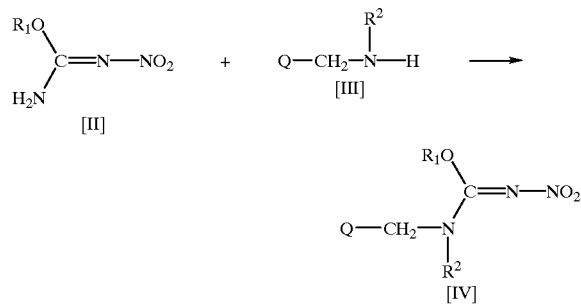

wherein each symbol has the same meaning as defined above.

The compound [III] or a salt thereof is used in a proportion of about 0.5 to about 5 equivalents, and preferably about 0.7 to about 1.5 equivalents with respect to the amount of the compound [II] or a salt thereof, which is assumed from the case of isolating it, but either one of them may be used in a large excess amount in case of no obstruction for the reaction.

This reaction can advantageously proceed by adjusting the pH within a range from 5 to 8, more preferably from 6 to 7.5. In case of nitration with nitric acid in the presence of sulfuric acid, the pH may be adjusted in the above range by adding an alkaline substance because the reaction mixture becomes strongly acidic.

The alkaline substance includes alkali metal hydroxide such as sodium hydroxide, potassium hydroxide, etc.; alkalin earth metal hydroxide such as magnesium hydroxide, barium hydroxide, etc.; metal carbonate such as sodium carbonate, potassium carbonate, magnesium carbonate, etc.; and alkali metal hydrogencarbonate such as sodium hydrogencarbonate, potassium hydrogencarbonate, etc. The pH may be adjusted after adding the compound [III] or a salt thereof, but the mixture is neutralized before adding the compound [III] or a salt thereof and the pH may be adjusted accurately after adding the compound [III] or a salt thereof. When the pH varies during the reaction, the pH may be adjusted in the preferable range at an appropriate time. The reaction is more preferably conducted by adjusting the pH using an aqueous 25 to 50% sodium hydroxide solution as the alkaline substance without newly adding any solvent. However, it is possible to add water or the solvent as described in the above reaction (a) which does not interfere with the reaction.

The reaction temperature is normally from about -20 to about 250° C., and preferably from about -10 to about 50° C. The reaction time is normally in a range from about 30 minutes to about 4 weeks, and preferably from about 2 hours to about 7 days.

The compound [IV] or a salt thereof thus obtained can be isolated and purified by a known means, for example, concentration, concentration under reduced pressure, distillation, fractional distillation, solvent extraction, pH change, redistribution, chromatography, crystallization, recrystallization and the like.

The compounds [II] and [IV] or salts thereof forms cis- and trans-stereoisomers for the position of the nitro group, the compounds [II] and [IV] theoretically form tautomers depending on the substituents, and all these isomers are also included in the corresponding compounds [II] and [IV] or salts thereof.

The compounds [I] or salts thereof used as the starting materials in the above method of present invention are known compounds, and can be produced according to methods described in e.g. Chemiker-Zeitung, Vol.98, pp.617, 1974 and JP-A-157358/1991. The compound [I] or a salt thereof may be used as it is after isolation/purification, or may be used in the subsequent nitration reaction in the state of the crude compound or reaction mixture. In case of using O-methylisourea monomethyl sulfate as the starting material, this compound can be obtained by the reaction between urea and dimethyl sulfate (Journal of Chemical Society, Vol.1955, pp.3551), and the reaction mixture is preferably subjected to the nitration reaction as it is.

The compound [III] or a salt thereof can be produced according to a per se known method or a similar method thereof. Said method includes, for example, methods described in Organic Functional Group Preparations, Academic Press, Vol.1, Sec.13, 1968; supra Vol.3, Sec.10, 1972 and JP-A-171/1990.

A guanidine derivative having an excellent insecticidal activity can be derived from the compound [IV] or a salt thereof produced by the present production method according to a method described in WO97/00867.

[Industrial Applicability]

According to the production method of the present invention, a compound [IV] as an intermediate of a guanidine derivative having an excellent insecticidal activity, or a salt thereof can be mass-produced, industrially. Specifically, the compound [IV] or a salt thereof can be obtained in a high yield without requiring a complicated operation, and safety of the operation can be remarkably improved.

EXAMPLES

The following Examples further illustrate the present invention but are not to be construed to limit the scope thereof.

Proton NMR spectra (Hu 1H-NMR) were measured by using a Bruker AC-200P type spectrometer and all δ values were represented by ppm using tetramethylsilane as an internal standard.

Furthermore, abbreviations used in the following Examples and Comparative Examples have the following meanings:

S: singlet, br: broad, d: doublet, t: triplet, J: coupling constant, Hz: Hertz, DMSO-$d_6$: deutero-dimethyl sulfoxide, %: % by weight, Mp.: melting point. The term "room temperature" used herein means a temperature ranging from about 15 to 25° C.

Reference 1

To a mixture obtained by dissolving O-methylisourea 1/2 sulfate (hereinafter, sometimes abbreviated as OMIU-S) (3.57 g 29.0 mmol) in 97% sulfuric acid (13.7 ml, 9 eq.), 97% nitric acid (3.72 ml, 3 eq.) was added dropwise over 10 minutes at room temperature. After stirring for 1 hour, the reacting solution was added to ice (100 g). The resulting mixture was neutralized by adding 40% aqueous sodium hydroxide solution and then extracted with ethyl acetate (100 ml×3). The extracts were dried over anhydrous magnesium sulfate and concentrated under reduced pressure to obtain 3.09 g of O-methyl-N-nitroisourea (MNI) in a yield of 89.6%. $^1$H-NMR (DMSO-$d_6$): 3.76 (3H, s), 8.60–9.20 (2H, br. s). Mp.107–109° C.

Reference 2

98% Sulfuric acid (353 kg, 3527.1 mol) was charged in a 500 L reactor and OMIU-S (120 kg, 974.7 mol) was added. 98% nitric acid (111 kg, 1726.4 mol) was added dropwise at 4–5° C. over 3 hours. The temperature was raised to 24° C. over 0.5 hour and the mixture was stirred at 24–27° C. for 2.5 hours. 880 kg of water and 880 kg of ice were charged in a 3000 L reactor and the reacting solution was poured in the reactor at −9 to 0° C. over 1 hour. The resulting mixture was stirred at −2 to −12° C. overnight and the crystal was deposited at −12° C. for 1.5 hours. The resulting crystal was collected by filtration with centrifugation and then washed with 10 kg of water to obtain 98 kg of a wet crystal.

336 kg of water was charged in a 500 L reactor and the wet crystal previously collected by filtration was added to water. 6.5 kg of an aqueous 30% sodium hydroxide solution was added dropwise at 7 to 10° C. over 0.5 hours to adjust the pH to 7.95. The resulting mixture was stirred at 10 to 12° C. for 1 hour and then subjected to centrifugal filtration, and washed with 5 kg of water to obtain 83 kg of a wet crystal. The wet crystal was dried at 60° C. to obtain 77.1 kg of MNI (purity 99.4%, yield 66.4%).

Reference 3

Urea [99%] (3.03 g, 0.05 mol) and dimethyl sulfate [95%] (6.64 g, 0.05 mol) were mixed at room temperature and the mixture was stirred in a few minutes. The mixture was heated in an oil bath and stirred at 80° C. for 24 hours. After cooling to room temperature, sulfuric acid [95%, d 1.84] (11.2 ml, 0.2 mol) was added to the mixture and the mixture was further cooled to 5° C. Fuming nitric acid [97%, d 1.52] (6.4 ml, 0.15 mol) was added dropwise to the mixture over 25 minutes while maintaining the internal temperature to below 10° C. The ice bath was then removed and the temperature was gradually raised to room temperature. After stirring for total 2 hours, the mixture was poured into ice-water (60 g–40 g), neutralized by adding an aqueous 30% sodium hydroxide solution and extracted with ethyl acetate (80 ml×3), and then the extracts were dried over anhydrous magnesium sulfate and concentrated. The residue was washed with isopropyl ether to obtain 3.25 g (54.6%) of MNI as a white crystal.

Reference 4

5-(Aminomethyl)-2-chlorothiazole (1.49 g, 10.0 mmol) was dissolved in diluted hydrochloric acid (15 ml, 10.0 mmol), and MNI (1.31 g, 11.0 mmol) was added to it. At that time, the pH was 2.1. The pH was adjusted to 6.2 with an aqueous sodium hydroxide solution(0.1 N, 4 ml) (using a pH meter), 1 ml of water was added to make the total volume to 20 ml, and then the mixture was stirred at room temperature for 16 hours. At that time, the pH increased to 7.1. The deposited white crystal was collected by filtration under reduced pressure and then washed with water. The resultant was dried under reduced pressure (80° C., 2 hours) to obtain 1.62 g (yield 64.6%) of O-methyl-N-(2-chloro-5-thiazolylmethyl)-N'-nitroisourea.

$^1$H-NMR (DMSO-$d_6$): 3.87 (3H, s), 4.61 (2H, d, J=5.5 Hz), 7.61 (1H, s), 9.90 (1H, br. t, J=5.5 Hz). Mp.133–135° C.

Example 1

Sulfuric acid [95%, d 1.84] (14 ml, 0.25 mol) was added to OMIU-S (8.61 g, 0.05 mol) under cooling and the mixture was further cooled to 5° C. Fuming nitric acid [97%, d 1.52] (6.4 ml, 0.15 mol) was added dropwise to the mixture over 1 hour while maintaining the internal temperature at below 8° C. The ice bath was then removed and the temperature was gradually raised to room temperature. After stirring for total 2 hours, the mixture was poured into ice-water (60 g–40 g) and an aqueous 40% sodium hydroxide solution was added to neutralize (pH 2) so as not to increase the pH to more than 4.5-(Aminomethyl)-2-chlorothiazole (5.65 g, 0.038 mol) was added and the mixture was stirred at room temperature for 48 hours while adjusting the pH to about 6.7 with an aqueous sodium hydroxide solution. The deposited crystal was collected by filtration, washed with water and then dried to obtain 6.63 g of O-methyl-N-(2-chloro-5-thiazolylmethyl)-N'-nitroisourea. The yield was 69.6% based on 5-(aminomethyl)-2-chlorothiazole, and 52.9% based on OMIU-S.

Example 2

OMIU-S (6.2 g, 0.0504 mol) was dissolved in concentrated sulfuric acid (15.5 g, 95%, 0.15 mol) cooled to below 10° C. and then the temperature of the solution was adjusted to 20° C. and fuming nitric acid (6.5 g, 97%, 0.10 mol) was gradually added and the solution was left to stand for 2 hours to complete the nitration. This solution was poured into 50 g of water cooled to below 10° C. to obtain a white suspension, and then 57.15 g of a 28% sodium hydroxide solution was added to adjust the pH to 5.0. Then, 5-(aminomethyl)-2-chlorothiazole.1/2 sulfate (9.05 g, 0.0458 mol) was poured and the temperature of the mixture was adjusted to 20° C., and then the pH of the mixture was adjusted to 6.5 by adding 1% sodium hydroxide solution. This solution was left to stand with maintaining at 20° C. for 40 hours and the pH was adjusted to 7.2 by adding a 1% sodium hydroxide solution. The temperature of the mixture was raised to 40° C., maintained for 4 hours, and then the mixture was left to stand at 10° C. for 2 hours and the resulting crystal was collected by filtration. The crystal was dried under reduced pressure at 45° C. to obtain 7.4 g of O-methyl-N-(2-chloro-5-thiazolylmethyl)-N'-nitroisourea as a pale yellowish white crystal. The yield was 64.5% based on 5-(aminomethyl)-2-chlorothiazole, and 58.7% based on OMIU-S.

Example 3

Urea [99%] (3.03 g, 0.05 mol) and dimethyl sulfate [95%](6.64 g, 0.05 mol) were mixed at room temperature and stirred for a few minutes. The mixture was heated in an oil bath and stirred at 80° C. for 15 hours. The mixture was cooled to room temperature and sulfuric acid [95%, d 1.84] (11.2 ml, 0.2 mol) was added, and then the mixture was further cooled to 5° C. Fuming nitric acid [97%, d 1.52] (6.4 ml, 0.15 mol) was added dropwise over 25 minutes while maintaining the interior temperature to below 10° C. Then, the ice bath was removed and the temperature was gradually raised to room temperature. After stirring for total 2 hours, the mixture was poured into ice-water (60 g–40 g) and neutralized (about pH 2) by adding an aqueous 40% sodium hydroxide solution. 5-(Aminomethyl)-2-chlorothiazole (3.34 g, 0.023 mol) was added (pH 3.8) and then the pH was adjusted to about 6.7 with 40% aqueous sodium hydroxide solution, and then the mixture was stirred at room temperature for 20 hours. The deposited crystal was collected by filtration, washed and then dried to obtain 3.63 g of O-methyl-N-(2-chloro-5-thiazolylmethyl)-N'-nitroisourea. The yield was 64.4%. based on 5-(aminomethyl)-2-chlorothiazole, and 29.0% based on urea.

Example 4

OMIU-S (124 g, 1.01 mol) was added portionwise to concentrated sulfuric acid (95%) (313 g, 3.03 mol) while cooling to 5 to 10° C. with stirring. When stirring at the same temperature for 30 minutes, all was dissolved. Then, fuming nitric acid (97%) (108 ml, 164.1 g, 2.52 mol) was added dropwise over 30 minutes. Subsequently, the mixture was heated to 25 to 30° C. and stirred for 2 hours. The pressure was reduced to 40–50 mmHg for 2 hours while heating and stirring the mixture on a water bath at 40° C. 50 ml of water was separately cooled to 5 to 10° C. and stirred, and then the reaction mixture obtained above was added dropwise over 30 minutes. The vessel of the reaction mixture was washed with 20 ml of water and the washing was added dropwise. The mixture was neutralized by adding 137 ml of an aqueous 28% sodium hydroxide solution. The pH at that time was 8.46. Subsequently, the pH was adjusted to 4.5 to 5.5 by adding a 5% sulfuric acid solution and then 53.0 g of an aqueous 5-(aminomethyl)-2-chlorothiazole hydrochloride solution (0.092 mol) (32.1% as 5-(aminomethyl)-2-chlorothiazole hydrochloride) was added over 20 minutes. The temperature was raised to 20° C. and the pH was adjusted to 7.00 to 7.20 by adding 10 ml of water and 12 ml of 1% aqueous sodium hydroxide solution, and then the mixture was stirred for 22 hours. The pH at that time was 7.40. The mixture was stirred for additional 21 hours and then the deposited crystal was collected by filtration, washed twice with 100 ml of water of 30° C.

The resulting wet crystal was dried at 60° C. under reduced pressure in the presence of phosphorous pentoxide overnight to obtain 17.4 g (yield 75.5%) of O-methyl-N-(2-chloro-5-thiazolylmethyl)-N'-nitroisourea as a pale yellow crystal.

Example 5

OMIU-S (12.4 g, 0.101 mol) was added portionwise to concentrated sulfuric acid (95%) (31.3 g, 0.303 mol) while cooling to 5–10° C. with stirring. When stirring at the same temperature for 30 minutes, all was dissolved. Then, fuming nitric acid (97%) (10.8 ml, 16.4 g, 0.252 mol) was added dropwise over 30 minutes. Subsequently, the mixture was heated to 25 to 30° C. and stirred for 2 hours.

100 ml of water was separately cooled to 5 to 10° C. and stirred, and then the reaction mixture obtained above was added dropwise over 30 minutes while bubbling air in a rate of 75 ml/min using an air pump. The vessel of the reaction mixture was washed with 20 ml of water and the washing was added dropwise. The mixture was neutralized by adding 131 ml of an aqueous 28% sodium hydroxide solution over 2 hours. The pH at that time was 6.95. Air was also continuously bubbled during the neutralization. Subsequently, an aqueous 5-(aminomethyl)-2-chlorothiazole hydrochloride solution (47.8 g, 0.0842 mol) (32.6% as 5-(aminomethyl)-2-chlorothiazole hydrochloride) was added over 20 minutes. The temperature was raised to 15° C. and the pH was adjusted to 7 by adding 20 ml of an aqueous 1% sodium hydroxide solution, and then the mixture was stirred for 30 hours. Then, the pH was adjusted to 7.2 with an aqueous 1% sodium hydroxide solution and the mixture was stirred for 12 hours at 25° C. The deposited crystal was collected by filtration, washed twice with 80 ml of water of 30° C. The resulting wet crystal was dried under reduced pressure in the presence of phosphorous pentoxide at 60° C. overnight to obtain 15.08 g (yield 71.4%) of O-methyl-N-(2-chloro-5-thiazolylmethyl)-N'-nitroisourea as a colorless crystal.

What is claimed is:

1. A method for producing a compound represented by the formula:

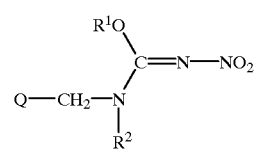

[IV]

or a salt thereof, wherein $R^1$ represents an optionally substituted hydrocarbon group; $R^2$ represents a hydrogen atom or an optionally substituted hydrocarbon group; and Q represents an optionally substituted heterocyclic group, which comprises:

subjecting a compound represented by the formula:

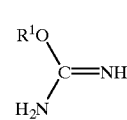

[I]

or a salt thereof, wherein $R^1$ has the same meaning as defined above, to a nitration reaction (a), to obtain a mixture containing a compound represented by the formula:

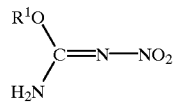

[II]

or a salt thereof, wherein $R^1$ has the same meaning as defined above, and further subjecting the mixture without isolating or purifying the compound represented by the formula [II] or salt thereof to a reaction (b) with a compound represented by the formula:

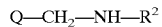

Q—CH$_2$—NH—R$^2$      [III]

or a salt thereof, wherein Q and $R^2$ have the same meaning as defined above, to obtain the compound represented by the formula [IV].

2. The method as claimed in claim 1, wherein the nitration reaction (a) is carried out by using nitric acid in the presence of sulfuric acid.

3. The method as claimed in claim 1, wherein a degassing treatment under reduced pressure is carried out after the completion of the nitration reaction (a).

4. The methods as claimed in claim 1, wherein the reaction mixture is diluted with water and/or ice after the completion of nitration reaction (a), and then subjected to the reaction (b).

5. The method as claimed in claim 4, wherein a gas which does not interfere with the reaction is bubbled during the dilution of the reaction mixture with water and/or ice.

6. The method as claimed in claim 5, wherein the gas which does not interfere with the reaction is air or nitrogen.

7. The method as claimed in claim 4, wherein the reaction (b) is carried out under pH 5 to 8.

8. The method as claimed in claim 4, wherein the reaction (b) is carried out under pH 6 to 7.5.

9. The method as claimed in claim 1, wherein $R^1$ is a $C_{1-3}$ alkyl group.

10. The method as claimed in claim 1, wherein the compound represented by the formula [I] or a salt thereof is O-methylisourea sulfate, O-methylisourea 1/2 sulfate or O-methylisourea monomethyl sulfate.

11. The method as claimed in claim 1, wherein $R^2$ is a hydrogen atom and Q is a 6-chloro-3-pyridyl group or a 2-chloro-5-thiazolyl group.

\* \* \* \* \*